United States Patent
Broglie

(12)
(10) Patent No.: US 6,429,358 B1
(45) Date of Patent: Aug. 6, 2002

(54) CORN PULLULANASE

(75) Inventor: Karen E. Broglie, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/403,618

(22) PCT Filed: May 4, 1998

(86) PCT No.: PCT/US98/09102

§ 371 (c)(1),
(2), (4) Date: Nov. 5, 1999

(87) PCT Pub. No.: WO98/50562

PCT Pub. Date: Nov. 12, 1998

Related U.S. Application Data

(60) Provisional application No. 60/045,723, filed on May 6, 1997.

(51) Int. Cl.[7] .................. C12N 15/82; C12N 15/29; A01H 5/00; A01H 5/10; C12P 19/04
(52) U.S. Cl. ............... 800/284; 800/278; 536/23.6; 435/69.1; 435/101; 435/210; 435/320.1; 435/419; 435/468
(58) Field of Search .................. 800/278, 284; 536/23.6; 435/69.1, 101, 210, 320.1, 419, 468

(56) References Cited

U.S. PATENT DOCUMENTS

| 5,514,576 A | 5/1996 | Bower ................ 435/210 |
| 5,912,413 A | * 6/1999 | Myers et al. ............. 800/205 |
| 6,300,115 B1 | 10/2001 | Teague et al. ............. 435/210 |

FOREIGN PATENT DOCUMENTS

| WO | WO 95/06128 | 3/1995 | ........... C12N/15/82 |
| WO | WO 95/09922 | 4/1995 | ........... C12N/15/62 |
| WO | WO 96/03513 | 2/1996 | ........... C12N/15/55 |
| WO | WO 96/19581 | 6/1996 | ........... C12N/15/56 |
| WO | WO 97/32985 | 9/1997 | ........... C12N/15/56 |

OTHER PUBLICATIONS

Nakamura, et al, "Rice mRNA for Starch Debranching Enzyme (R–enzyme), Complete cds," *EMBL Nucleotide Sequence*, XP002034077, May 30, 1995.
Renz et al, "S.oleracea L. mRNA for Pullulanase", *EMBL Nucleotide Sequence*, XP00200114, Jan. 19, 1995.
James, et al, "Characterization of the Maize Gene sugary1, a Determinant of Starch Composition in Kernels", *The Plant Cell*, 7, 417–429, Apr. 1995.
Manners, et al, "Studies on Carbohydrate–Metabolising Enzymes", *Carbohydrate Research*, 9, 107–121, Jan. 1, 1969.
Doehlert, et al, "Two Classes of Starch Debranching Enzymes from Developing Maize Kernels", *Plant Physiology*, 138, 566–571, 1991.
Shyamala, et al, "Genome Walking by Single–Specific–Primer Polymerase Chain Reaction: SSP–PCR", *Gene*, 84, 1–8, 1989.
Meijer, et al, "Isolation of Cytochrome P–450 cDNA clones from the Higher Plant *Catharanthus Roseus* by a PCR Strategy", *Plant Molecular Biology*, 22, 379–383, 1993.
Smith, A. et al (1995) Plant Physiol. 107:673–677.
Preiss, J. (1988) Biochemistry of Plants 14:181–253.
Walker, C.E. (1988) Cereal Foods World 33:491–494.
Nakamura, Y. et al. (1996) Planta 199(2):209–218.
Renz, A. et al. (1995) EMBL Accession No. 1076269.

* cited by examiner

*Primary Examiner*—David T. Fox

(57) ABSTRACT

This invention relates to isolated nucleic acid fragments encoding all or a substantial portion of a corn pullulanase. The invention also relates to the construction of chimeric genes encoding all or a portion of a corn pullulanase, in sense or antisense orientation, wherein expression of the chimeric gene results in production of altered levels of corn pullulanase in a transformed host cell.

11 Claims, 3 Drawing Sheets

Identities = 682/877 (77%), Positives = 770/877 (87%), Gaps = 29/877 (3%)

```
Query:   5  DARAYWVTKSLIAWNISDQKTSLFLYASRNATMCMSSQDMKGYDSKVELQPENDGLPSSV  184
            DARAYWVT+SLIAWN++DQ TSLFLYASR+ATM +S   + GYDSK+EL+PE+  LP +V
Sbjct:  84  DARAYWVTRSLIAWNVNDQDTSLFLYASRDATMHVSDGAIHGYDSKIELEPEHASLPDNV  143

Query: 185  TQKFPFISSYRAFRIPSSVDVATLVKCQLAVASFDAHGNRQDVTGLQLPGVLDDMFAYTG  364
            +KFPFI SYR FR+PSSVDVA+LVKCQLAVAS+DAHG  QDVTGLQLPGVLDDMFAYTG
Sbjct: 144  AEKFPFIRSYRTFRVPSSVDVASLVKCQLAVASYDAHGRHQDVTGLQLPGVLDDMFAYTG  203

Query: 365  PLGTISSEEAVSMYLWAPTAQDVSVSFYDGPAGPLLETVQLNELNGVWSVTGPRNWENRY  544
            PLG + S++ V +YLWAPTAQDV V FYDGPAGPLL+TVQL ELNGVWSVT PR  EN+Y
Sbjct: 204  PLGAVFSDKDVDLYLWAPTAQDVRVCFYDGPAGPLLQTVQLKELNGVWSVTVPRYPENQY  263

Query: 545  YLYEVTVYHQTTGNIEKCLAADPYARGLSANSTRTWLVDINNETLKPLAWDGLAAEKPRL  724
            YLYEV VYH +T  +EKCLA DPYARGLSAN TRTWLVDIN+ETLKP +WD L+ E+P L
Sbjct: 264  YLYEVKVYHPSTSQVEKCLADDPYARGLSANGTRTWLVDINSETLKPASWDELSDEEPNL  323

Query: 725  DSFSDISIYELHIRDFSAHDSTVDCPFRGGFCAFTF------------------------  832
            +SFSDISIYELHIRDFSAHDSTVDC  RGGF    F
Sbjct: 324  ESFSDISIYELHIRDFSAHDSTVDCNSRGGFVHLHFRLFRLNLLNDFCSPPITKHPGRIM  383

Query: 833  ----QDSVGIEHLKKLSDAGLTHVHLLPSFQFGGVDDIKSNWKCVDEIELSKLPPGSDLQ 1000
                QDS GI HL+KLS AGLTHVHLLPSF  F  VDD KSNWK VDE +L+KLPPGSD Q
Sbjct: 384  ETVMQDSAGIRHLRKLSAAGLTHVHLLPSFHFASVDDNKSNWKFVDEAQLAKLPPGSDEQ  443
```

FIG. 1A

```
Query: 1001  QAAIVAIQEEDPYNWGYNPVVWGVPKGSYASNPDGPSRIIEYRLMVQALNRLGLRVVMDV  1180
             QAAIV+IQ+EDPYNWGY+PV+WGVPKGSYASNPDGPSRIIEYR MVQALNR+GLRVVMDV
Sbjct:  444  QAAIVSIQQEDPYNWGYDPVLWGVPKGSYASNPDGPSRIIEYRQMVQALNRIGLRVVMDV   503

Query: 1181  VYNHLYSSGPFAITSVLDKIVPGYYLRRDSNGQTENSAAVNNTASEHFMVDRLIVDDLLN  1360
             VYNHL SSGPF  ++SVLDKIVPGYYLRR+ NGQ ENSAA+NNTASEHFMVDRL VDDLLN
Sbjct:  504  VYNHLDSSGPFGVSSVLDKIVPGYYLRRNVNGQIENSAAMNNTASEHFMVDRLTVDDLLN   563

Query: 1361  WAVNYKVDGFRFDLMGHIMKKTMIRAKSALQSLTIDEHGVDGSKIYLYGEWNFGEVAEN   1540
             WA+NYKVDGFRFDLMGHIMK TMIRAKSA++SLT D HGV GSKIYLYGEGW+FGEVA+N
Sbjct:  564  WAINYKVDGFRFDLMGHIMKSTMIRAKSAIRSLTRDVHGVYGSKIYLYGEGWDFGEVAQN   623

Query: 1541  QRGINGSQLKMSGTGIGSFNDRIRDAINGGSPFGNPLQQGFSTGLFLEPNGFYQGNETET  1720
             +RGIN SQ+ MSGTGIGSFNDRIRD++NGG+PFGNPLQQGFSTGLFLEPNG+YQGNE +T
Sbjct:  624  KRGINASQINMSGTGIGSFNDRIRDSVNGGNPFGNPLQQGFSTGLFLEPNGYYQGNEADT   683

Query: 1721  RLTLATYADHIQIGLAGNLKDYVVISHTGEARKGSEIRTFDGSPVGYASSPIETINYASA  1900
             R  LATYADHIQIGLAGNLKDYV+  +HTGEA+KGS+I TFDGSPVGY SSP+ETINY SA
Sbjct:  684  RRELATYADHIQIGLAGNLKDYVLRTHTGEAKKGSDIYTFDGSPVGYTSSPVETINYVSA   743

Query: 1901  HDNETLFDIISLKTPMDLSIDERCRINHLSTSMIALSQGIPFFHAGDEILRSKSLDRDSY  2080
             HDNETLFDI+S+KTP+ LSID   CRINHL++SMIALSQGIPFFHAGDEILRSKSLDRDSY
Sbjct:  744  HDNETLFDIVSIKTPIGLSIDGECRINHLASSMIALSQGIPFFHAGDEILRSKSLDRDSY   803
```

FIG. 1B

```
Query:  2081  DSGDWFNKIDFTYETNNWGVGLP-PREKNEGSWPLMKPRLENPSFKPAKHDIIAALDKFI  2257
              +SGDWF K+D        N  +G   +E   +   L+KPRLENPSF+P K+ I++  D F+
Sbjct:   804  NSGDWFKKLDLHM---NQPIGCRLLQEIRMKNMHLIKPRLENPSFRPLKNHILSCFDNFV   860

Query:  2258  DILKIRYSSPLFRLTTASDIVQRVHFHNTGPSLVPGVIVMSIEDARNDRHDMAQIDETFS  2437
              DILKIRYSSPLFRL+TASDI QRV FHNTGPS+VPGVIVMSI+DA+N++     MAQ+D+ FS
Sbjct:   861  DILKIRYSSPLFRLSTASDIEQRVRFHNTGPSMVPGVIVMSIKDAQNEKCKMAQLDKNFS   920

Query:  2438  CVVTVFNVCPYEVSIEIPDLASLRLQLHPVQVNSSDALARQSAYDTATGRFTVPKRTAAV  2617
              VVT+FNVCP+EVSIEI DLASL L+LHP+QVNSSDAL RQSAY+ + GRFTVP+RT AV
Sbjct:   921  YVVTIFNVCPHEVSIEIHDLASLGLELHPIQVNSSDALVRQSAYEASKGRFTVPRRTTAV   980

Query:  2618  FVEPRC  2635
              FV+PRC
Sbjct:   981  FVQPRC   986
```

FIG. 1C

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 624 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
CTCAGAAGGG ACTCTAATGG TCAGACTGAG AACAGCGCGG CTGTGAACAA TACAGCAAGT      60

GAGCATTTCA TGGTTGATAG ATTAATCGTG GATGACCTTC TGAATTGGGC AGTAAATTA      120

AAAGTTGACG GGTTCAGATT TGATCTAATG GGACATATCA TGAAAAAGAC AATGATTAG      180

GCAAAATCGG CTCTTCAAAG CCTTACAATT GATGAACATG GAGTAGATGG TTCAAAGAT      240

TACTTGTATG GTGAAGGATG GAACTTCGGT GAAGTTGCGG AAAATCAACG TGGGATAAA      300

GGATCCCAGC TAAAAATGAG TGGCACTGGG ATTGGTAGTT TCAACGATAG AATCCGTGA      360
```

```
GCTATAAATG GTGGCAGTCC GTTTGGGAAT CCACTGCAAC AAGGTTTCTC TACTGGATT     420

TTCTTAGAGC CAAATGGATT TTATCAGGGC AATGAAACAG AGACAAGGCT CACGCTTGC     480

ACATACGCTG ACCATATACA GATTGGATTA GCTGGCAATT TGAAGGACTA TGTAGTTAT     540

TCTCATACTG GAGAAGCTAG AAAANGATCT GAAATTTCGC ACCTTCGATG GCTCACCAG     600

TNGGCTATGC TTCATCCCCT ATAN                                           624
```

(2) INFORMATION FOR SEQ ID NO: 2:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Leu Arg Arg Asp Ser Asn Gly Gln Thr Glu Asn Ser Ala Ala Val Asn
1               5                   10                  15

Asn Thr Ala Ser Glu His Phe Met Val Asp Arg Leu Ile Val Asp Asp
            20                  25                  30

Leu Leu Asn Trp Ala Val Asn Tyr Lys Val Asp Gly Phe Arg Phe Asp
        35                  40                  45

Leu Met Gly His Ile Met Lys Lys Thr Met Ile Arg Ala Lys Ser Ala
    50                  55                  60

Leu Gln Ser Leu Thr Ile Asp Glu His Gly Val Asp Gly Ser Lys Ile
65                  70                  75                  80

Tyr Leu Tyr Gly Glu Gly Trp Asn Phe Gly Glu Val Ala Glu Asn Gln
                85                  90                  95

Arg Gly Ile Asn Gly Ser Gln Leu Lys Met Ser Gly Thr Gly Ile Gly
            100                 105                 110

Ser Phe Asn Asp Arg Ile Arg Asp Ala Ile Asn Gly Gly Ser Pro Phe
        115                 120                 125

Gly Asn Pro Leu Gln Gln Gly Phe Ser Thr Gly Leu Phe Leu Glu Pro
    130                 135                 140

Asn Gly Phe Tyr Gln Gly Asn Glu Thr Glu Thr Arg Leu Thr Leu Ala
145                 150                 155                 160

Thr Tyr Ala Asp His Ile Gln Ile Gly Leu Ala Gly Asn Leu Lys Asp
                165                 170                 175

Tyr Val Val Ile Ser His Thr Gly Glu Ala Arg Lys Xaa Ser Glu Ile
            180                 185                 190

Ser His Leu Arg Trp Leu Thr Ser Xaa Ala Met Leu His Pro Leu Xaa
        195                 200                 205
```

(2) INFORMATION FOR SEQ ID NO: 3:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CCTTAGACAA ATTTATTGAT ATCCTCAAGA TCAGATACTC ATCACCTCTC TTTCGCCTAA     60

CTACAGCAAG TGATATTGTG CAAAGGGTTC ACTTTCACAA CACAGGGCCC TCCTTGGTT     120
```

```
CAGGAGTTAT TGTCATGAGC ATCGAAGATN ANCGAAATGA TAGGCATGAT ATGGCCCAG     180

TAGATGAAAC ATTCTCTTGT GTCGTTACAG TCTTCAATGT ATGTCCGTAC GAAGTGTCT     240

TAGAAATCCC TGATCTTGCA TCACTGCGGC TTCAGTTGCA TCCAGTGCAG GTGAATTCA     300

CGGATGCGTT AGCCAGGCAG TCTGCGTACG ACACCGCCAC AGGTCGATTC ACCGTGCCG     360

AAAGGACAGC AGCAGTGTTC GTGGAACCCA GGTGCTGATG GATGCCTTTC GCTAGCGAG     420

AAGTGCATTC GGCATCCAAG TCGAAGCAAA CGAATGANAT AAGAGAAGGC CATCGAATA     480

AACG                                                                484
```

(2) INFORMATION FOR SEQ ID NO: 4:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Leu Asp Lys Phe Ile Asp Ile Leu Lys Ile Arg Tyr Ser Ser Pro Leu
1               5                   10                  15

Phe Arg Leu Thr Thr Ala Ser Asp Ile Val Gln Arg Val His Phe His
            20                  25                  30

Asn Thr Gly Pro Ser Leu Val Pro Gly Val Ile Val Met Ser Ile Glu
        35                  40                  45

Asp Xaa Arg Asn Asp Arg His Asp Met Ala Gln Ile Asp Glu Thr Phe
    50                  55                  60

Ser Cys Val Val Thr Val Phe Asn Val Cys Pro Tyr Glu Val Ser Ile
65                  70                  75                  80

Glu Ile Pro Asp Leu Ala Ser Leu Arg Leu Gln Leu His Pro Val Gln
                85                  90                  95

Val Asn Ser Ser Asp Ala Leu Ala Arg Gln Ser Ala Tyr Asp Thr Ala
            100                 105                 110

Thr Gly Arg Phe Thr Val Pro Lys Arg Thr Ala Ala Val Phe Val Glu
        115                 120                 125

Pro Arg Cys
    130
```

(2) INFORMATION FOR SEQ ID NO: 5:

(i) SEQUENCE CHARACTERISTICS:
        (A) LENGTH: 986 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Met Gln Met Leu Leu His Ala Asn Ser Leu Leu Leu Leu Ala Pro Thr
1               5                   10                  15

Thr Ser Arg Leu Ser Ala Ser Ala Ser Pro Gly Arg Ser Gly Thr Ala
            20                  25                  30

Arg Pro Leu Pro Pro Pro Gln Gly Thr Arg Ile Pro Pro Ala Pro Pro
            35                  40                  45

Leu Ala Gly His Gly Gly Arg Pro Pro Ser Pro Gln Pro Arg Arg Gly
        50                  55                  60
```

```
Arg Asp Gly Val Gly Glu Glu Cys Ala Ala Val Ala Ser Gln Gly
 65              70                  75                  80

Phe Val Thr Asp Ala Arg Ala Tyr Trp Val Thr Arg Ser Leu Ile Ala
            85                  90                  95

Trp Asn Val Asn Asp Gln Asp Thr Ser Leu Phe Leu Tyr Ala Ser Arg
            100                 105                 110

Asp Ala Thr Met His Val Ser Asp Gly Ala Ile His Gly Tyr Asp Ser
            115                 120                 125

Lys Ile Glu Leu Glu Pro Glu His Ala Ser Leu Pro Asp Asn Val Ala
130                 135                 140

Glu Lys Phe Pro Phe Ile Arg Ser Tyr Arg Thr Phe Arg Val Pro Ser
145                 150                 155                 160

Ser Val Asp Val Ala Ser Leu Val Lys Cys Gln Leu Ala Val Ala Ser
            165                 170                 175

Tyr Asp Ala His Gly Arg His Gln Asp Val Thr Gly Leu Gln Leu Pro
            180                 185                 190

Gly Val Leu Asp Asp Met Phe Ala Tyr Thr Gly Pro Leu Gly Ala Val
            195                 200                 205

Phe Ser Asp Lys Asp Val Asp Leu Tyr Leu Trp Ala Pro Thr Ala Gln
    210                 215                 220

Asp Val Arg Val Cys Phe Tyr Asp Gly Pro Ala Gly Pro Leu Leu Gln
225                 230                 235                 240

Thr Val Gln Leu Lys Glu Leu Asn Gly Val Trp Ser Val Thr Val Pro
                245                 250                 255

Arg Tyr Pro Glu Asn Gln Tyr Tyr Leu Tyr Glu Val Lys Val Tyr His
            260                 265                 270

Pro Ser Thr Ser Gln Val Glu Lys Cys Leu Ala Asp Asp Pro Tyr Ala
            275                 280                 285

Arg Gly Leu Ser Ala Asn Gly Thr Arg Thr Trp Leu Val Asp Ile Asn
            290                 295                 300

Ser Glu Thr Leu Lys Pro Ala Ser Trp Asp Glu Leu Ser Asp Glu Glu
305                 310                 315                 320

Pro Asn Leu Glu Ser Phe Ser Asp Ile Ser Ile Tyr Glu Leu His Ile
                325                 330                 335

Arg Asp Phe Ser Ala His Asp Ser Thr Val Asp Cys Asn Ser Arg Gly
            340                 345                 350

Gly Phe Val His Leu His Phe Arg Leu Phe Arg Leu Asn Leu Leu Asn
            355                 360                 365

Asp Phe Cys Ser Pro Pro Ile Thr Lys His Pro Gly Arg Ile Met Glu
    370                 375                 380

Thr Val Met Gln Asp Ser Ala Gly Ile Arg His Leu Arg Lys Leu Ser
385                 390                 395                 400

Ala Ala Gly Leu Thr His Val His Leu Leu Pro Ser Phe His Phe Ala
            405                 410                 415

Ser Val Asp Asp Asn Lys Ser Asn Trp Lys Phe Val Asp Glu Ala Gln
            420                 425                 430

Leu Ala Lys Leu Pro Pro Gly Ser Asp Glu Gln Gln Ala Ala Ile Val
            435                 440                 445

Ser Ile Gln Gln Glu Asp Pro Tyr Asn Trp Gly Tyr Asp Pro Val Leu
450                 455                 460

Trp Gly Val Pro Lys Gly Ser Tyr Ala Ser Asn Pro Asp Gly Pro Ser
465                 470                 475                 480
```

-continued

```
Arg Ile Ile Glu Tyr Arg Gln Met Val Gln Ala Leu Asn Arg Ile Gly
                485                 490                 495
Leu Arg Val Val Met Asp Val Val Tyr Asn His Leu Asp Ser Ser Gly
            500                 505                 510
Pro Phe Gly Val Ser Ser Val Leu Asp Lys Ile Val Pro Gly Tyr Tyr
            515                 520                 525
Leu Arg Arg Asn Val Asn Gly Gln Ile Glu Asn Ser Ala Ala Met Asn
        530                 535                 540
Asn Thr Ala Ser Glu His Phe Met Val Asp Arg Leu Thr Val Asp Asp
545                 550                 555                 560
Leu Leu Asn Trp Ala Ile Asn Tyr Lys Val Asp Gly Phe Arg Phe Asp
                565                 570                 575
Leu Met Gly His Ile Met Lys Ser Thr Met Ile Arg Ala Lys Ser Ala
            580                 585                 590
Ile Arg Ser Leu Thr Arg Asp Val His Gly Val Tyr Gly Ser Lys Ile
        595                 600                 605
Tyr Leu Tyr Gly Glu Gly Trp Asp Phe Gly Glu Val Ala Gln Asn Lys
        610                 615                 620
Arg Gly Ile Asn Ala Ser Gln Ile Asn Met Ser Gly Thr Gly Ile Gly
625                 630                 635                 640
Ser Phe Asn Asp Arg Ile Arg Asp Ser Val Asn Gly Gly Asn Pro Phe
                645                 650                 655
Gly Asn Pro Leu Gln Gln Gly Phe Ser Thr Gly Leu Phe Leu Glu Pro
            660                 665                 670
Asn Gly Tyr Tyr Gln Gly Asn Glu Ala Asp Thr Arg Arg Glu Leu Ala
        675                 680                 685
Thr Tyr Ala Asp His Ile Gln Ile Gly Leu Ala Gly Asn Leu Lys Asp
        690                 695                 700
Tyr Val Leu Arg Thr His Thr Gly Glu Ala Lys Lys Gly Ser Asp Ile
705                 710                 715                 720
Tyr Thr Phe Asp Gly Ser Pro Val Gly Tyr Thr Ser Ser Pro Val Glu
                725                 730                 735
Thr Ile Asn Tyr Val Ser Ala His Asp Asn Glu Thr Leu Phe Asp Ile
            740                 745                 750
Val Ser Ile Lys Thr Pro Ile Gly Leu Ser Ile Asp Gly Glu Cys Arg
        755                 760                 765
Ile Asn His Leu Ala Ser Ser Met Ile Ala Leu Ser Gln Gly Ile Pro
        770                 775                 780
Phe Phe His Ala Gly Asp Glu Ile Leu Arg Ser Lys Ser Leu Asp Arg
785                 790                 795                 800
Asp Ser Tyr Asn Ser Gly Asp Trp Phe Lys Lys Leu Asp Leu His Met
                805                 810                 815
Asn Gln Pro Ile Gly Cys Arg Leu Leu Gln Glu Ile Arg Met Lys Asn
            820                 825                 830
Met His Leu Ile Lys Pro Arg Leu Glu Asn Pro Ser Phe Arg Pro Leu
        835                 840                 845
Lys Asn His Ile Leu Ser Cys Phe Asp Asn Phe Val Asp Ile Leu Lys
        850                 855                 860
Ile Arg Tyr Ser Ser Pro Leu Phe Arg Leu Ser Thr Ala Ser Asp Ile
865                 870                 875                 880
Glu Gln Arg Val Arg Phe His Asn Thr Gly Pro Ser Met Val Pro Gly
                885                 890                 895
Val Ile Val Met Ser Ile Lys Asp Ala Gln Asn Glu Lys Cys Lys Met
```

```
                    900                 905                 910
Ala Gln Leu Asp Lys Asn Phe Ser Tyr Val Val Thr Ile Phe Asn Val
            915                 920                 925

Cys Pro His Glu Val Ser Ile Glu Ile His Asp Leu Ala Ser Leu Gly
930                 935                 940

Leu Glu Leu His Pro Ile Gln Val Asn Ser Ser Asp Ala Leu Val Arg
945                 950                 955                 960

Gln Ser Ala Tyr Glu Ala Ser Lys Gly Arg Phe Thr Val Pro Arg Arg
            965                 970                 975

Thr Thr Ala Val Phe Val Gln Pro Arg Cys
            980                 985

(2) INFORMATION FOR SEQ ID NO: 6:

(i) SEQUENCE CHARACTERISTICS:
        (A) LENGTH: 964 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Met Ser Ser Leu Tyr Asn Pro Ile Ala Leu Ala Ser Ser Phe His His
1               5                   10                  15

His Tyr Pro Asn Leu Arg Phe Leu Pro Phe Asn Phe Asn Phe Ile Thr
            20                  25                  30

Lys Leu Pro Val Ser Asn Ser Phe Ala Ile Gly Ser Ser Ser Arg Ser
            35                  40                  45

Phe His Ser Ser Pro Leu Lys Lys Asp Ser Ser Cys Phe Cys Cys Ser
50                  55                  60

Met Ala Val Glu Val Gly Ser Ala Ser Ser Val Ser Gln Ser Glu Leu
65                  70                  75                  80

Gln Gly Ser Leu Asn Ser Cys Arg Ala Tyr Trp Pro Ser Lys Tyr Thr
                85                  90                  95

Phe Ala Trp Asn Val Asp Ile Gly Asn Gly Ser Tyr Tyr Leu Phe Ala
            100                 105                 110

Ser Lys Thr Ala Ala Leu Lys Phe Thr Asp Ala Gly Ile Glu Gly Tyr
            115                 120                 125

Asp Val Lys Ile Lys Leu Asp Lys Asp Gln Gly Gly Leu Pro Ala Asn
130                 135                 140

Val Thr Glu Lys Phe Pro His Ile Arg Gly Tyr Ser Ala Phe Lys Ala
145                 150                 155                 160

Pro Ala Thr Leu Asp Val Asp Ser Leu Leu Lys Cys Gln Leu Ala Val
            165                 170                 175

Ala Ala Phe Ser Ala Asp Gly Ala Cys Arg Asn Ala Thr Gly Leu Gln
            180                 185                 190

Leu Pro Gly Val Ile Asp Glu Leu Tyr Ser Tyr Asp Gly Pro Leu Gly
            195                 200                 205

Ala Val Phe Ser Glu Asn Thr Ile Ser Leu Tyr Leu Trp Ala Pro Thr
            210                 215                 220

Ala Gln Ala Val Ser Ala Ser Ile Phe Lys Asp Pro Ser Gly Gly Glu
225                 230                 235                 240

Pro Leu Gln Thr Val Gln Leu Ile Glu Ser Asn Gly Val Trp Ser Ala
            245                 250                 255

Val Gly Pro Arg Thr Trp Glu Gly Cys Tyr Tyr Val Tyr Glu Ile Thr
```

-continued

```
                  260                 265                 270
    Val Tyr His His Ser Thr Leu Arg Ile Glu Lys Ser Phe Ala Ile Asp
                  275                 280                 285
    Pro Tyr Ala Arg Gly Ile Ser Ala Asp Val Lys Arg Thr Leu Leu Ala
                  290                 295                 300
    Asp Leu Ser Ser Glu Thr Leu Lys Pro Glu Gly Trp Glu Asn Leu Ala
    305                 310                 315                 320
    Asp Glu Lys Pro His Leu Leu Ser Pro Ser Asp Ile Ser Leu Tyr Glu
                  325                 330                 335
    Leu His Ile Arg Asp Phe Ser Ala Tyr Asp Leu Thr Val His Pro Asp
                  340                 345                 350
    Leu Arg Gly Gly Tyr Leu Ala Phe Thr Ser Gln Asp Ser Ala Gly Val
                  355                 360                 365
    Asn His Leu Glu Lys Leu Ser Ala Ala Gly Leu Thr His Val His Leu
                  370                 375                 380
    Leu Pro Ser Phe Gln Phe Ala Glu Val Asp Asp Lys Lys Lys Trp
    385                 390                 395                 400
    Lys Phe Val Asp Thr Lys Arg Phe Glu Thr Leu Pro Pro Asp Ser Glu
                  405                 410                 415
    Glu Gln Gln Ala Gln Ile Thr Ala Ile Arg Asp Glu Asp Gly Tyr Asn
                  420                 425                 430
    Trp Gly Tyr Asn Pro Val Leu Trp Gly Thr Pro Lys Gly Ser Tyr Ala
                  435                 440                 445
    Thr Asp Pro Asn Gly Pro Cys Arg Ile Ile Glu Phe Arg Lys Met Val
                  450                 455                 460
    Gln Ala Leu Asn Arg Ile Gly Leu Arg Val Val Leu Asp Val Val Tyr
    465                 470                 475                 480
    Asn His Leu Asn Ser Ser Gly Pro Ser Asp Asp Asn Ser Val Leu Asp
                  485                 490                 495
    Lys Ile Val Pro Gly Tyr Tyr Leu Arg Arg Asp Asn Asp Gly Ala Ile
                  500                 505                 510
    Glu Asn Ser Thr Cys Val Asn Asp Thr Ala Ser Glu His Phe Met Val
                  515                 520                 525
    Glu Arg Leu Ile Leu Asp Asp Leu Lys His Trp Ala Val Asn Tyr Lys
                  530                 535                 540
    Val Asp Gly Phe Arg Phe Asp Leu Met Gly His Ile Met Lys His Thr
    545                 550                 555                 560
    Met Val Lys Ala Thr Asn Met Leu Gln Gly Leu Ser Lys Asn Ile Asp
                  565                 570                 575
    Gly Val Glu Gly Ser Ser Ile Tyr Leu Tyr Gly Glu Gly Trp Asp Phe
                  580                 585                 590
    Gly Glu Val Ala Asn Asn Ala Arg Gly Val Asn Ala Ser Gln Leu Asn
                  595                 600                 605
    Leu Gly Gly Thr Gly Ile Gly Ser Phe Asn Asp Arg Ile Arg Asp Ala
                  610                 615                 620
    Val Leu Gly Gly Gly Pro Phe Gly Pro Pro Leu Gln Gln Gly Tyr Val
    625                 630                 635                 640
    Thr Gly Leu Ser Leu Gln Pro Asn Asp His Asp His Ser Gly Lys Ala
                  645                 650                 655
    Asn Ala Asp Arg Met Leu Ala Val Ala Lys Asp His Ile Gln Val Gly
                  660                 665                 670
    Met Ala Gly Asn Leu Arg Asp Tyr Ile Leu Thr Asn Cys Asp Gly Lys
                  675                 680                 685
```

Gln Val Lys Gly Ser Glu Val Tyr Thr Tyr Gly Thr Pro Val Gly
690                 695                 700

Tyr Ala Met Gln Pro Ile Glu Thr Ile Asn Tyr Val Ser Ala His Asp
705                 710                 715                 720

Asn Glu Thr Leu Phe Asp Ile Val Ser Leu Lys Thr Pro Thr Tyr Ile
                725                 730                 735

Thr Val Asp Glu Arg Cys Arg Val Asn His Leu Ala Thr Ser Ile Leu
                740                 745                 750

Ala Leu Ser Gln Gly Ile Pro Phe Phe His Ala Gly Asp Glu Leu Leu
                755                 760                 765

Arg Ser Lys Ser Leu Asp Arg Asp Ser Tyr Asn Ser Gly Asp Trp Phe
770                 775                 780

Asn Arg Leu Asp Phe Ser Tyr Asn Ser Asn Asn Trp Gly Val Gly Leu
785                 790                 795                 800

Pro Pro Lys Asp His Asn Glu Ser Asn Trp Pro Leu Ile Lys Lys Arg
                805                 810                 815

Leu Ala Asn Pro Ser Tyr Lys Pro Asp Lys Asn His Ile Ile Ala Ala
                820                 825                 830

Val Glu Asn Phe Thr Asn Leu Leu Gln Ile Arg Tyr Ser Ser Pro Leu
835                 840                 845

Phe Arg Leu Arg Ser Ala Lys Asp Ile Glu Asp Arg Val Arg Phe His
850                 855                 860

Asn Asn Val Pro Ser Trp Ile Pro Gly Leu Ile Ala Met Ser Ile Glu
865                 870                 875                 880

Asp Gly His Ala Gly Ala Pro Gly Leu Ser Gln Ile Asp Pro Lys Phe
                885                 890                 895

Gln Tyr Ile Val Val Ile Asn Val Gln Pro Thr Glu Thr Lys Phe
                900                 905                 910

Val Asn Pro Asp Leu Arg Ala Lys Ser Leu Gln Leu His Pro Val Gln
                915                 920                 925

Ser Thr Ser Gly Asp Thr Val Val Lys Glu Ser Lys Tyr Glu Pro Ser
930                 935                 940

Thr Gly Cys Phe Thr Ile Pro Pro Lys Ser Thr Ala Val Phe Val Glu
945                 950                 955                 960

Pro Arg His Val (2) INFORMATION FOR SEQ ID NO: 7:

(i) SEQUENCE CHARACTERISTICS:
        (A) LENGTH: 2904 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GTTGGATGCG AGGGCTTACT GGGTGACAAA ATCCTTGATT GCATGGAATA TCAGTGATCA    60

GAAAACTTCT CTCTTCTTAT ATGCAAGCAG AAATGCTACA ATGTGCATGT CGAGTCAGG   120

TATGAAAGGT TATGATTCCA AAGTTGAGCT GCAACCAGAA AATGATGGAC TTCCATCCA   180

TGTGACCCAG AAATTCCCTT TTATCAGCTC TTATAGAGCC TTCAGAATTC CGAGCTCCG   240

TGATGTTGCC ACCTTGGTGA AATGTCAACT TGCTGTTGCT TCATTTGATG CTCATGGGA   300

CAGGCAAGAT GTTACTGGGT TGCAACTACC TGGAGTATTG GATGACATGT TCGCCTACA   360

```
TGGACCGCTT GGTACTATTT CTAGTGAAGA AGCTGTGAGT ATGTACCTAT GGGCTCCTA      420

AGCACAGGAT GTAAGTGTGA GCTTCTATGA TGGTCCAGCT GGCCCTTTAC TGGAAACAG      480

TCAACTCAAC GAGTTAAATG GTGTTTGGAG TGTTACTGGT CCAAGGAACT GGGAGAACC      540

GTATTATCTA TATGAAGTCA CAGTATATCA TCAAACTACA GGAAACATTG AGAAATGTT      600

AGCCGCTGAT CCTTATGCTA GAGGGCTTTC TGCAAATAGC ACACGAACTT GGTTGGTTG      660

TATTAATAAT GAAACATTAA AGCCACTTGC CTGGGATGGA TTGGCGGCTG AAAAGCCAA      720

GCTTGATTCC TTCTCTGACA TAAGCATATA TGAATTGCAC ATTCGTGATT TCAGTGCCC      780

TGATAGCACA GTGGACTGTC CTTTCCGAGG AGGTTTCTGT GCATTTACAT TTCAGGATT      840

TGTAGGCATA GAACACCTAA AGAAACTATC TGATGCCGGT TTGACTCATG TCCATTTGT      900

GCCAAGCTTT CAATTTGGTG GTGTTGATGA CATAAAGAGC AATTGGAAAT GTGTTGATG      960

GATTGAACTG TCAAAACTCC CTCCAGGGTC AGATTTGCAA CAAGCTGCAA TTGTGGCT      1020

TCAGGAAGAG GACCCTTATA ATTGGGGGTA TAACCCTGTG GTTTGGGGCG TTCCAAAA      1080

AAGCTATGCA AGTAACCCAG ATGGTCCAAG TCGTATCATT GAGTACCGGC TGATGGTG      1140

GGCCTTGAAT CGCTTAGGTC TTCGAGTTGT CATGGATGTT GTATACAATC ATCTATAC      1200

AAGTGGCCCT TTTGCCATCA CTTCCGTGCT TGACAAGATT GTACCTGGAT ACTACCTC      1260

AAGGGACTCT AATGGTCAGA CTGAGAACAG CGCGGCTGTG AACAATACAG CAAGTGAG      1320

TTTCATGGTT GATAGATTAA TCGTGGATGA CCTTCTGAAT TGGGCAGTAA ATTACAAA      1380

TGACGGGTTC AGATTTGATC TAATGGGACA TATCATGAAA AAGACAATGA TTAGAGCA      1440

ATCGGCTCTT CAAAGCCTTA CAATTGATGA ACATGGAGTA GATGGTTCAA AGATATAC      1500

GTATGGTGAA GGATGGAACT TCGGTGAAGT TGCGGAAAAT CAACGTGGGA TAAATGGA      1560

CCAGCTAAAA ATGAGTGGCA CTGGGATTGG TAGTTTCAAC GATAGAATCC GTGATGCT      1620

AAATGGTGGC AGTCCGTTTG GGAATCCACT GCAACAAGGT TTCTCTACTG GATTGTTC      1680

AGAGCCAAAT GGATTTTATC AGGGCAATGA AACAGAGACA AGGCTCACGC TTGCTACA      1740

CGCTGACCAT ATACAGATTG GATTAGCTGG CAATTTGAAG GACTATGTAG TTATATCT      1800

TACTGGAGAA GCTAGAAAAG GATCTGAAAT TCGCACCTTC GATGGCTCAC CAGTTGGC      1860

TGCTTCATCC CCTATAGAAA CAATAAACTA CGCCTCTGCT CATGACAATG AAACACTA      1920

TGATATTATT AGTCTAAAGA CTCCGATGGA CCTCTCAATT GACGAGCGAT GCAGGATA      1980

TCATTTGTCC ACAAGCATGA TTGCATTATC CCAGGGAATA CCATTTTTTC ATGCTGGT      2040

TGAGATACTA CGATCTAAGT CGCTTGATCG AGATTCATAT GACTCTGGTG ATTGGTTT      2100

CAAGATTGAT TTTACCTATG AAACAAACAA TTGGGGTGTT GGGCTTCCAC CAAGAGAA      2160

GAACGAAGGG AGCTGGCCTT TGATGAAGCC AAGATTGGAG AACCCGTCGT TCAAACCT      2220

AAAACATGAC ATTATTGCTG CCTTAGACAA ATTTATTGAT ATCCTCAAGA TCAGATAC      2280

ATCACCTCTC TTTCGCCTAA CTACAGCAAG TGATATTGTG CAAAGGGTTC ACTTTCAC      2340

CACAGGGCCC TCCTTGGTTC CAGGAGTTAT TGTCATGAGC ATCGAAGATG CACGAAAT      2400

TAGGCATGAT ATGGCCCAGA TAGATGAAAC ATTCTCTTGT GTCGTTACAG TCTTCAAT      2460

ATGTCCGTAC GAAGTGTCTA TAGAAATCCC TGATCTTGCA TCACTGCGGC TTCAGTTG      2520

TCCAGTGCAG GTGAATTCAT CGGATGCGTT AGCCAGGCAG TCTGCGTACG ACACCGCC      2580

AGGTCGATTC ACCGTGCCGA AAAGGACAGC AGCAGTGTTC GTGGAACCCA GGTGCTGA      2640

GATGCCTTTC GCTAGCGAGC AAGTGCATTC GGCATCCAAG TCGAAGCAAA CGAATGAA      2700

GATGCCTTTC GCTAGCGAGC AAGTGCATTC GGCATCCAAG TCGAAGCAAA CGAATGAA      2700

AAGAGAAGGC CATCGAATAA AACGAAGTAT ATAAATAGAT TGAATAAGAC GTTGCCCA      2760
```

```
TTGCCAAGGC ACGCTTTGCC ATATGTATGC GTTGAAAAAT AAATAAATAA ATAAATAA      2820

GATGTTATAG AGGTACAAAA GCATTGGAAC ATTTCTTTAT AGAGGTGAAC CACCCTAT      2880

TCCAAAAAAA AAAAAAAAAA AAAA                                          2904
```

(2) INFORMATION FOR SEQ ID NO: 8:

(i) SEQUENCE CHARACTERISTICS:
        (A) LENGTH: 878 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 8:

```
Leu Asp Ala Arg Ala Tyr Trp Val Thr Lys Ser Leu Ile Ala Trp Asn
 1               5                  10                  15

Ile Ser Asp Gln Lys Thr Ser Leu Phe Leu Tyr Ala Ser Arg Asn Ala
                20                  25                  30

Thr Met Cys Met Ser Ser Gln Asp Met Lys Gly Tyr Asp Ser Lys Val
            35                  40                  45

Glu Leu Gln Pro Glu Asn Asp Gly Leu Pro Ser Ser Val Thr Gln Lys
        50                  55                  60

Phe Pro Phe Ile Ser Ser Tyr Arg Ala Phe Arg Ile Pro Ser Ser Val
65                  70                  75                  80

Asp Val Ala Thr Leu Val Lys Cys Gln Leu Ala Val Ala Ser Phe Asp
                85                  90                  95

Ala His Gly Asn Arg Gln Asp Val Thr Gly Leu Gln Leu Pro Gly Val
            100                 105                 110

Leu Asp Asp Met Phe Ala Tyr Thr Gly Pro Leu Gly Thr Ile Ser Ser
        115                 120                 125

Glu Glu Ala Val Ser Met Tyr Leu Trp Ala Pro Thr Ala Gln Asp Val
130                 135                 140

Ser Val Ser Phe Tyr Asp Gly Pro Ala Gly Pro Leu Leu Glu Thr Val
145                 150                 155                 160

Gln Leu Asn Glu Leu Asn Gly Val Trp Ser Val Thr Gly Pro Arg Asn
                165                 170                 175

Trp Glu Asn Arg Tyr Tyr Leu Tyr Glu Val Thr Val Tyr His Gln Thr
            180                 185                 190

Thr Gly Asn Ile Glu Lys Cys Leu Ala Ala Asp Pro Tyr Ala Arg Gly
        195                 200                 205

Leu Ser Ala Asn Ser Thr Arg Thr Trp Leu Val Asp Ile Asn Asn Glu
    210                 215                 220

Thr Leu Lys Pro Leu Ala Trp Asp Gly Leu Ala Ala Glu Lys Pro Arg
225                 230                 235                 240

Leu Asp Ser Phe Ser Asp Ile Ser Ile Tyr Glu Leu His Ile Arg Asp
                245                 250                 255

Phe Ser Ala His Asp Ser Thr Val Asp Cys Pro Phe Arg Gly Gly Phe
            260                 265                 270

Cys Ala Phe Thr Phe Gln Asp Ser Val Gly Ile Glu His Leu Lys Lys
        275                 280                 285

Leu Ser Asp Ala Gly Leu Thr His Val His Leu Leu Pro Ser Phe Gln
    290                 295                 300

Phe Gly Gly Val Asp Asp Ile Lys Ser Asn Trp Lys Cys Val Asp Glu
305                 310                 315                 320
```

```
Ile Glu Leu Ser Lys Leu Pro Pro Gly Ser Asp Leu Gln Gln Ala Ala
            325                 330                 335

Ile Val Ala Ile Gln Glu Glu Asp Pro Tyr Asn Trp Gly Tyr Asn Pro
            340                 345                 350

Val Val Trp Gly Val Pro Lys Gly Ser Tyr Ala Ser Asn Pro Asp Gly
            355                 360                 365

Pro Ser Arg Ile Ile Glu Tyr Arg Leu Met Val Gln Ala Leu Asn Arg
            370                 375                 380

Leu Gly Leu Arg Val Val Met Asp Val Val Tyr Asn His Leu Tyr Ser
385                 390                 395                 400

Ser Gly Pro Phe Ala Ile Thr Ser Val Leu Asp Lys Ile Val Pro Gly
            405                 410                 415

Tyr Tyr Leu Arg Arg Asp Ser Asn Gly Gln Thr Glu Asn Ser Ala Ala
            420                 425                 430

Val Asn Asn Thr Ala Ser Glu His Phe Met Val Asp Arg Leu Ile Val
            435                 440                 445

Asp Asp Leu Leu Asn Trp Ala Val Asn Tyr Lys Val Asp Gly Phe Arg
450                 455                 460

Phe Asp Leu Met Gly His Ile Met Lys Lys Thr Met Ile Arg Ala Lys
465                 470                 475                 480

Ser Ala Leu Gln Ser Leu Thr Ile Asp Glu His Gly Val Asp Gly Ser
            485                 490                 495

Lys Ile Tyr Leu Tyr Gly Glu Gly Trp Asn Phe Gly Glu Val Ala Glu
            500                 505                 510

Asn Gln Arg Gly Ile Asn Gly Ser Gln Leu Lys Met Ser Gly Thr Gly
            515                 520                 525

Ile Gly Ser Phe Asn Asp Arg Ile Arg Asp Ala Ile Asn Gly Gly Ser
            530                 535                 540

Pro Phe Gly Asn Pro Leu Gln Gln Gly Phe Ser Thr Gly Leu Phe Leu
545                 550                 555                 560

Glu Pro Asn Gly Phe Tyr Gln Gly Asn Glu Thr Glu Thr Arg Leu Thr
            565                 570                 575

Leu Ala Thr Tyr Ala Asp His Ile Gln Ile Gly Leu Ala Gly Asn Leu
            580                 585                 590

Lys Asp Tyr Val Val Ile Ser His Thr Gly Glu Ala Arg Lys Gly Ser
            595                 600                 605

Glu Ile Arg Thr Phe Asp Gly Ser Pro Val Gly Tyr Ala Ser Ser Pro
            610                 615                 620

Ile Glu Thr Ile Asn Tyr Ala Ser Ala His Asp Asn Glu Thr Leu Phe
625                 630                 635                 640

Asp Ile Ile Ser Leu Lys Thr Pro Met Asp Leu Ser Ile Asp Glu Arg
            645                 650                 655

Cys Arg Ile Asn His Leu Ser Thr Ser Met Ile Ala Leu Ser Gln Gly
            660                 665                 670

Ile Pro Phe Phe His Ala Gly Asp Glu Ile Leu Arg Ser Lys Ser Leu
            675                 680                 685

Asp Arg Asp Ser Tyr Asp Ser Gly Asp Trp Phe Asn Lys Ile Asp Phe
            690                 695                 700

Thr Tyr Glu Thr Asn Asn Trp Gly Val Gly Leu Pro Pro Arg Glu Lys
705                 710                 715                 720

Asn Glu Gly Ser Trp Pro Leu Met Lys Pro Arg Leu Glu Asn Pro Ser
            725                 730                 735
```

-continued

```
Phe Lys Pro Ala Lys His Asp Ile Ile Ala Ala Leu Asp Lys Phe Ile
        740             745             750

Asp Ile Leu Lys Ile Arg Tyr Ser Ser Pro Leu Phe Arg Leu Thr Thr
        755             760             765

Ala Ser Asp Ile Val Gln Arg Val His Phe His Asn Thr Gly Pro Ser
    770             775             780

Leu Val Pro Gly Val Ile Val Met Ser Ile Glu Asp Ala Arg Asn Asp
785             790             795                         800

Arg His Asp Met Ala Gln Ile Asp Glu Thr Phe Ser Cys Val Val Thr
            805             810                     815

Val Phe Asn Val Cys Pro Tyr Glu Val Ser Ile Glu Ile Pro Asp Leu
            820             825             830

Ala Ser Leu Arg Leu Gln Leu His Pro Val Gln Val Asn Ser Ser Asp
        835             840             845

Ala Leu Ala Arg Gln Ser Ala Tyr Asp Thr Ala Thr Gly Arg Phe Thr
    850             855             860

Val Pro Lys Arg Thr Ala Ala Val Phe Val Glu Pro Arg Cys
865             870             875
```

CORN PULLULANASE

CROSS-REFERENCE TO RELATED APPLICATIONS

This application is a 371 of PCT/US98/09102 filed May 4, 1998, which claims priority to provisional application Ser. No. 60/045,723 filed May 6, 1997.

FIELD OF THE INVENTION

This invention is in the field of plant molecular biology. More specifically, this invention pertains to nucleic acid fragments encoding enzymes involved in starch biosynthesis in corn plants and seeds.

BACKGROUND OF THE INVENTION

Corn starch is an important component of food, feed, and industrial products. Broadly speaking, it consists of two types of glucan polymers: relatively long chained polymers with few branches known as amylose, and shorter chained but highly branched molecules called amylopectin. Its biosynthesis depends on the complex interaction of multiple enzymes (Smith, A. et al., (1995) *Plant Physiol.* 107:673–677; Preiss, J., (1988) *Biochemistry of Plants* 14:181–253). Chief among these are ADP-glucose pyrophosphorylase, which catalyzes the formation of ADP-glucose, a series of starch synthases which use ADP glucose as a substrate for polymer formation using α-1–4 linkages; and several starch branching enzymes, which modify the polymer by transferring segments of polymer to other parts of the polymer using α-1–6 linkages, creating branched structures. However, based on data from other starch forming plants such as potato, and on corn mutants, it is becoming clear that other enzymes also play a role in the determination of the final structure of starch. In particular, debranching enzymes such as isoamylase and pullulanase, and disproportionating enzymes not only participate in starch degradation, but also in modification of starch structure during its biosynthesis. Different models for this action have been proposed, but all share the concept that such activities, or lack thereof, change the structure of the starch produced.

This is of applied interest because changes in starch structure, such as the relative amounts of amylose and amylopectin or the degree and length of branching of amylopectin, alter its function in cooking and industrial processes. For example, starch derived from different naturally occurring mutants of corn can be shown on the one hand to differ in structure and correspondingly to differ in functional assays such as Rapid Visco analysis, which measures changes in viscosity as starch is heated and then cooled (Walker, C. E., (1988) *Cereal Foods World* 33:491–494). The interplay of different enzymes to produce different structures, and in turn how different structures correlate with different functionalities, is not yet completely understood. However, it is understood that changing starch structure will result in alteration in starch function which can in turn lead to new applications or reduced processing costs (certain starch functionalities can at present only be attained through expensive chemical modification of the starch).

The role of debranching enzymes in starch biosynthesis, in particular in affecting the degree of branching, indicates that over-expression or reduction of expression of such genes in corn could be used to alter branch chain distribution of corn starch. While pullulanase genes have been described from other plants (U.S. Pat. No. 5,514.576: Nakamura. Y. et al., (1996) *Plunta* 199(2):209–218; Renz. A. et al., (1995) EMBL Accession No. 1076269), a pullulanase gene has yet to be described for corn.

SUMMARY OF THE INVENTION

The instant invention relates to isolated nucleic acid fragments encoding a corn pullulanase. In addition, this invention relates to nucleic acid fragments that are complementary to nucleic acid fragments encoding a corn pullulanase.

In another embodiment, the instant invention relates chimeric genes encoding a corn pullulanase or nucleic acid fragments that are complementary to nucleic acid fragments encoding a corn pullulanase, operably linked to suitable regulatory sequences, wherein expression of the chimeric gene results in production of altered levels of corn pullulanase in a transformed host cell.

In a further embodiment, the instant invention concerns a transformed host cell comprising in its genome a chimeric gene encoding a corn pullulanase, operably linked to suitable regulatory sequences, wherein expression of the chimeric gene results in production of altered levels of corn pullulanase in the transformed host cell. The transformed host cells can be of eukaryotic or prokaryotic origin, and include cells derived from higher plants and microorganisms. The invention also includes transformed plants that arise from transformed host cells of higher plants, and from seeds derived from such transformed plants.

An additional embodiment of the instant invention concerns a method of altering the level of expression of corn pullulanase in a transformed host cell comprising: a) transforming a host cell with the chimeric gene encoding a corn pullulanase, operably linked to suitable regulatory sequences; and b) growing the transformed host cell under conditions that are suitable for expression of the chimeric gene wherein expression of the chimeric gene results in production of altered levels of corn pullulanase in the transformed host cell.

An addition embodiment of the instant invention concerns a method for obtaining a nucleic acid fragment encoding all or substantially all of an amino acid sequence encoding a plant pullulanase.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows an alignment of the amino acid sequence of the instant corn pullulanase enzyme set forth in SEQ ID NO:8 (subject) with that of the *Oryza sativa* pullulanase set forth in GenBank Accession No. D50602 (Query).

SEQ ID NO:1 is the nucleotide sequence of cDNA clone cen3n.pk0028.d2 encoding a portion of a corn pullulanase.

SEQ ID NO:2 is the deduced amino acid sequence obtained from translation of the nucleotide sequence of cDNA clone cen3n.pk0028.d2.

SEQ ID NO:3 is the nucleotide sequence of cDNA clone cen3n.pk0031.h9 encoding a portion of a corn pullulanase.

SEQ ID NO:4 is the deduced amino acid sequence obtained from translation of the nucleotide sequence of cDNA clone cen3n.pk0031.h9.

SEQ ID NO:5 is the amino acid sequence encoding the *Oryza sativa* pullulanase having DDBJ Accession No. D50602.

SEQ ID NO:6 is the amino acid sequence encoding the *Spinacia oleracea* pullulanase having GenBank accession No. X83969.

SEQ ID NO:7 is the nucleotide sequence of cDNA clone encoding a portion of a corn pullulanase.

SEQ ID NO:8 is the deduced amino acid sequence obtained from translation of the nucleotide sequence of cDNA clone encoded by SEQ ID NO:7.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the corn pullulanase protein as set forth in SEQ ID NOs:2, 4 and 8. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence. and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding: sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

cDNA clones encoding a corn pullulanase gene have been isolated and identified by comparison of random plant cDNA sequences to the GenBank database using the BLAST algorithms well known to those skilled in the art. The nucleotide sequences of these corn pullulanase cDNAs are provided in SEQ ID NOs:1 and 3, and the deduced amino acid sequences are provided in SEQ ID NOs:2 and 4. Pullulanase genes from other plants can now be identified by comparison of random cDNA sequences to the corn pullulanase sequences provided herein.

The nucleic acid fragments of the instant invention may be used to isolate cDNAs and genes encoding homologous pullulanase from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction). As described herein, a nucleic acid fragment encoding all or almost all of a corn pullulanase (SEQ ID NO:7) was isolated using a portion of the insert from a cDNA clone identified by comparison of random plant cDNA sequences to the GenBank database (cen3n.pk0028.d2; see Example 2).

For example, other pullulanase genes, either as cDNAs or genomic DNAs, could be isolated directly by using all or a portion of the instant corn pullulanase gene as a DNA hybridization probe to screen libraries from any desired plant employing methodology well known to those skilled in the art. Specific oligonucleotide probes based upon the instant pullulanase sequence can be designed and synthesized by methods known in the art (Maniatis). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequence. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous pullulanase genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding plant pullulanase. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Finally, availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which corn pullulanase is present at higher or lower levels than normal or in cell types or developmental stages in which it is not normally found. This would have the effect of altering starch structure in those cells.

Overexpression of corn pullulanase may be accomplished by first constructing a chimeric gene in which the corn pullulanase coding region is operably linked to a promoter capable of directing expression of a gene in the desired tissues at the desired stage of development. For reasons of convenience, the chimeric gene may comprise a promoter sequence and translation leader sequence derived from the same gene. 3' Non-coding sequences encoding transcription termination signals must also be provided. The instant chimeric genes may also comprise one or more introns in order to facilitate gene expression.

A plasmid vector comprising the instant chimeric gene is then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al.. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the pullulanase protein to different cellular compartments, or to facilitate its secretion from the cell. It is thus envisioned that the chimeric gene described above may be further supplemented by altering the coding sequence to encode pullulanase protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future. It may also be desirable to reduce or eliminate expression of the pullulanase gene in plants for some applications. In order to accomplish this, a chimeric gene designed for co-suppression of pullulanase can be constructed by linking the pullulanase gene or gene fragment to a plant promoter sequences. Alternatively, a chimeric gene designed to express antisense RNA for all or part of the pullulanase gene can be constructed by linking the pullulanase gene or gene fragment in reverse orientation to a plant promoter sequences. Either the co-suppression or antisense chimeric gene could be introduced into plants via transformation wherein expression of the endogenous pullulanase gene is reduced or eliminated.

Corn pullulanase protein produced in heterologous host cells, particularly in the cells of microbial hosts, can be used to prepare antibodies to the protein by methods well known to those skilled in the art. The antibodies are useful for detecting corn pullulanase protein in situ in cells or in vitro in cell extracts. Preferred heterologous host cells for production of corn pullulanase protein are microbial hosts. Microbial expression systems and expression vectors containing regulatory sequences that direct high level expression of foreign proteins are well known to those skilled in the art. Any of these could be used to construct chimeric genes for production of corn pullulanase. These chimeric genes could then be introduced into appropriate microorganisms via transformation to provide high level expression of corn pullulanase. An example of a vector for high level expression of corn pullulanase in a bacterial host is provided (Example 4).

All or a portion of the nucleic acid fragments of the instant invention may also be used as probes for genetically and physically mapping the genes that they are a part of, and as markers for traits linked to expression of corn pullulanase. Such information may be useful in corn breeding in order to develop lines with desired starch phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am.J.Hum.Genet.* 32:3 14–331).

The production and use of plant gene-derived probes for use in genetic mapping is described in R. Bernatzky, R. and Tanksley, S. D. (1986) *Plant Mol.Biol.Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, this is generally not necessary for mapping methods. Such information may be useful in corn breeding in order to develop lines with desired starch phenotypes.

EXAMPLES

The present invention is further defined in the following Examples, in which all parts and percentages are by weight and degrees are Celsius. unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of a Corn cDNA Library: Isolation and Sequencing of cDNA Clones

A cDNA library representing mRNA from corn endosperm tissue obtained twenty days after pollination from *Zea mays* LE392 corn plants was prepared. A cDNA library was prepared in a Uni-ZAP™ XR vector according to the manufacturer's protocol (Stratagene Cloning Systems, La Jolla, Calif.). Conversion of the Uni-ZAP™ XR library into a plasmid library was accomplished according to the protocol provided by Stratagene. Upon conversion, cDNA inserts were contained in the plasmid vector pBluescript. The cDNA library was normalized by essentially following the protocol disclosed in U.S. Pat. No. 5,482,845. cDNA inserts from randomly picked bacterial colonies containing recombinant pBluescript plasmids were amplified via polymerase chain reaction using primers specific for vector sequences flanking the inserted corn cDNA sequences. Amplified insert DNAs were sequenced in dye-primer sequencing reactions according to the protocol provided by Perkin-Elmer; the resulting products were analyzed using a Perkin-Elmer ABI PRISM™ 377 DNA Sequencer.

Example 2

Identification and Characterization of cDNA Clones cDNAs encoding a corn pullulanase were identified by conducting a BLAST (Basic Local Alignment Search Tool; Altschul, S. F., et al., (1990) *J Mol. Biol.* 215:403–410; see also www.ncbi.nlm.nih.gov/BLAST/) search for similarity to sequences contained in the GenBank database. The corn cDNA sequences obtained in Example 1 were analyzed for similarity to all publicly available DNA sequences contained in the GenBank Database using the BLASTN algorithm provided by the National Center for Biotechnology Information (NCBI). The DNA sequences were translated in all reading frames and compared for similarity to all publicly available protein sequences contained in the GenBank Database using the BLASTX algorithm (Gish. W. and States, D. J. (1993) *Nature Genetics* 3:266–272) provided by the NCBI.

The BLASTN search using clone cen3n.pk0028.d2 revealed similarity of the instant nucleotide sequence to a nucleotide sequence reported in U.S. Pat. No. 5,514,576 (GenBank Accession No. 120414; logP=164.96) to encode an *Oryza sativa* pullalanase enzyme.

The BLASTX search using clone cen3n.pk0028.d2 revealed similarity of the protein encoded by the cDNA to *Oryza sativa* (DDJB Accession No. D50602; logP=112.55) and *Spinacia oleracea* (GenBank Accession No. X83969; logP=81.36) pullulanase enzymes. SEQ ID NO:1 shows the nucleotide sequence of the pullulanase cDNA. The corresponding amino acid sequence of the pullulanase protein is shown in SEQ ID NO:2. The amino acid sequence of the instant corn pullulanase shows approximately 83 and 63% sequence identity to *Oryza sativa* and *Spinacia oleracea* pullulanase enzymes, respectively.

An additional cDNA clone encoding a distinct portion of a corn pullulanase enzyme was identified by the methods described above. A BLASTX search using clone cen3n.pk0031.h9 also revealed similarity of the protein encoded by the cDNA to *Oryza sativa* (DDJB Accession No. D50602; logP=60.74) and *Spinacia oleracea* (GenBank Accession No. X83969; logP=35.17) pullulanase enzymes. SEQ ID NO:3 shows the nucleotide sequence of this pullulanase cDNA. The corresponding deduced amino acid sequence is shown in SEQ ID NO:4. The amino acid sequence of the instant corn pullulanase shows approximately 77 and 55% sequence identity to *Oryza sativa* and *Spinacia oleracea* pullulanase enzymes, respectively.

A 1291 bp EcoRI fragment of the insert in cDNA clone cen3n.pk0028.d2 was used as a hybridization probe to screen for full length sequences of corn pullulanase in a maize endosperm cDNA library (mRNA was extracted 20 days After pollination). Approximately $2.8 \times 10^6$ pfu were transferred in duplicate to nitrocellulose membranes. The immobilized DNA was hybridized with the radiolabeled EcoRI fragment and filters were washed essentially as described in Maniatis. Eighteen putative positive clones were identified from this initial screen. One of these positive clones, pDBE6A, was found to contain the longest cDNA insert. This clone was purified and subjected to further characterization. The complete nucleotide sequence of the cDNA insert in pDBE6A is set forth in SEQ ID NO:7. The 2904 bp insert consists of a 2638 bp open reading frame encoding an 878 amino acid polypeptide (SEQ ID NO:8), followed by 245 bp of 3' untranslated DNA and a 21 bp polyA region. Alignment of the deduced amino acid sequence with that of rice pullulanase shows the two sequences to be 75% identical at the amino acid level (FIG. 1). Sequence alignments and percent identity calculations were performed using the algorithm described by Altschul et al.((1990) *J Mol. Biol.* 215:403–410). Sequence alignments and BLAST scores and probabilities indicate that the instant nucleic acid fragments encode a entire or nearly entire corn pullulanase enzyme.

Example 3

Expression of Chimeric Genes in Plant Cells

A chimeric gene comprising a corn pullulanase cDNA in sense orientation with respect to the maize 27 kD zein promoter that is located 5' to the corn pullulanase fragment, and the 10 kD zein 3' end that is located 3' to the corn pullulanase fragment, can be constructed. The corn pullulanase fragment of this gene may be generated by polymerase chain reaction (PCR) of a cDNA clone comprising the corn pullulanase using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 uL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 0.001% w/v gelatin, 200 mM dGTP, 200 mM dATP, 200 mM dTTP, 200 mM dCTP and 0.025 unit Amplitaq™ DNA polymerase. Reactions are carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 12301 Parklawn Drive, Rockville, Md. 20852), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U. S. Biochemical). The resulting plasmid construct would comprise a chimeric gene encoding, in the 5' to 3' direction, the maize 27 kD zein promoter, the corn pullulanase cDNA fragment, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C.. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2.4-D. After two weeks the tissue can be transferred to regeneration medium (Fromm et al., (1990) *Bio/Technology* 8:833–839).

Starch extracted from single seeds obtained from corn plants transformed with the chimeric gene can then be analyzed. Seeds can be steeped in a solution containing 1.0% lactic acid and 0.3% sodium metabisulfite. pH 3.8, held at 52° C. for 22–24 h. Seeds are then drained, rinsed and homogenized individually in 8–9 mL of a solution of 100 mM NaCl. Five mL of toluene are added to each tube and vigorously shaken twice for 6 minutes using a paint mixer. and allowed to settle for 30 minutes. Two mL of 100 mM NaCl is sprayed onto the solution, allowed to settle for 30 minutes, and the protein-toluene layer is aspirated off. The toluene wash step is repeated. Twelve mL water is added and shaken in a paint shaker for 45 seconds. This solution is centrifuged for 10 minutes and the water is removed. The water wash is repeated, followed by a final wash with 12 mL of acetone. After shaking and centrifugation steps, the acetone is drained and allowed to evaporate for 1 h. Starch extracts are incubated in a 40° C. oven overnight.

Extracted starches can be enzymatically debranched as follows. Seven mg of each starch sample is added to a screw cap test tube containing 1.1 mL of water. The tubes are heated to 120° C. for 30 minutes and then placed in a water bath at 45° C. Debranching solution can be prepared by diluting 50 $\mu$L of isoamylase (5×10$^6$ units/mL; Sigma) per mL of 50 mM NaOAc buffer, pH 4.5. Forty $\mu$L of debranching solution is added to each starch sample, and the samples are incubated in a water bath at 45° C. for 3 h. The debranching reaction is stopped by heating samples to 110° C. for 5 minutes. Debranched starch samples can then be lyophilized and redisolved in DMSO.

One hundred $\mu$L of each debranched starch can then be analyzed by gel permeation chromatography (GPC). One hundred $\mu$L of each debranched starch is injected and chromatographed by passage through two GPC columns (Mixed Bed-C; Polymer Labs) arranged in series. Chromatography is performed at 100° C. and samples are eluted with DMSO at a flow rate of 1.0 mL/min. Chromatographic samples are collected at 25 minute intervals. A refractive index detector (Waters) can be used for detection, and data can be collected and stored with the aid of a computer running Chemstation Software (version A.02.05; Hewlett-Packard).

Retention times of collected samples may then be compared to retention times of pullulan standards (380K, 100K, 23.7K, 5.8K, 728 and 180 mw). The proportion of the total starch is determined for twenty-four ranges of degree of polymerization (DP) spanning both the amylose and amylopectin portions of the chromatogram. The percentage area in appropriate DP ranges is used to determine values for A & B1, B2, B3 and B4+ chains of the amylopectin portion of the chromatogram. The proportion of the total area above DP 150 is used to determine amylose content.

Amylopectin is typically described by its distribution to branch chains in the molecule. The amylopectin molecule is comprised of alternating crystalline and amorphous regions. The crystalline region is where many of the branch points ($\alpha$1,6 linkages) occur, while the amorphous region is an area of little to no branching and few branch chains. The type of chain may be designated as A or B. A chains are unbranched and span a single crystalline region. B1 chains also span a single crystalline region but are branched. B2, B3 and B4+ chains are branched and span 2, 3 and 4 or more crystalline regions, respectively (Hizukuri (1986) *Carbohydrate Res.* 147:342–347). The relative area under the amylopectin portion of the chromatograms can be used to determine the area percentage of the A & B1, B2, B3 and B4+ chains.

Starches derived Fromm kernels of plants transformed with the chimeric gene can also be tested for functionality by techniques well known to those skilled in the art. For example, starch can be extracted from dry mature kernels from transformed plants. Fifteen g of kernels are weighed into a 50 mL Erlenmeyer flask and steeped in 50 mL of steep solution (same as above) for 18 h at 52° C. The kernels are drained and rinsed with water. The kernels are then homogenized using a 20 mm Polytron probe (Kinematica GmbH; Kriens-Luzern, Switzerland) in 50 mL of cold 50 mM NaCl. The homogenate is filtered through a 72 micron mesh screen. The filtrate is brought up to a total volume of 400 mL with 50 mM NaCl and an equal volume of toluene is added. The mixture is stirred with a magnetic stir bar for 1 h at sufficient speed to completely emulsify the two phases. The emulsion is allowed to separate overnight in a covered beaker. The upper toluene layer is aspirated from the beaker and discarded. The starch slurry remaining in the bottom of the beaker is resuspended, poured into a 250 mL centrifuge bottle and centrifuged 15 minutes at 25,000 RCF. The supernatant is discarded and the starch is washed sequentially with water and acetone by shaking and centrifuging as above. After the acetone wash and centrifugation the acetone is decanted and the starch allowed to dry overnight in a fume hood at room temperature.

A Rapid Visco Analyzer (Newport Scientific; Sydney, Australia) with high sensitivity option and Thermocline software can then be used for pasting curve analysis. For each line, 1.50 g of starch is weighed into the sample cup and 25 mL of phosphate/citrate buffer (pH 6.50) containing 1% NaCl was added. Pasting curve analysis can be performed using the following temperature profile: idle temperature 50° C., hold at 50° C. for 0.5 minutes, linear heating to 95° C. for 2.5 minutes, linear cooling to 50° C. over 4 minutes, hold at 50° C. for four minutes.

Results of the Rapid Visco Analyzer pasting analysis may demonstrate that the starch produced by lines transformed with the chimeric gene differ in its pasting properties both from normal dent starch. This result may demonstrate that the alteration of starch fine structure produced by altering expression of a corn pullulanase can create a starch of novel functionality.

Example 4

Expression of Chimeric Genes in Microbial Cells

A corn pullulanase cDNA can be inserted into the T7 *E. coli* expression vector pET24d (Novagen). Plasmid DNA containing the corn pullulanase CDNA may be appropriately digested to release a nucleic acid fragment encoding the corn pullulanase. This fragment may then be purified on a 1% NuSieve® GTG® low melting agarose gel (FMC®). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the corn pullulanase fragment using T4 DNA ligase (NEB). The corn pullulanase fragment containing the ligated adapters can be purified from the excess adapters using low melting agarose as described above. The vector pET24d is digested, dephosphorylated with alkaline phosphatase (NEB) and deproteinized with phenol/chloroform as described above. The prepared vector pET24d and corn pullulanase fragment can then be ligated at 16° C. for 15 hours followed by transformation into DH5 electrocompetent cells (GIBCO BRL). Transformants can be selected on agar plates containing 2×YT media and 50 µg/mL kanamycin. Transformants containing the corn pullulanase gene are then screened for the correct orientation with respect to pET24d T7 promoter by restriction enzyme analysis.

Clones in the correct orientation with respect to the T7 promoter can be transformed into BL21(DE3) competent cells (Novagen) and selected on 2×YT agar plates containing 50 µg/ml kanamycin. A colony arising from this transformation construct can be grown overnight at 30° C. in 2×YT media with 50 µg/mL kanamycin. The culture is then diluted two fold with fresh media; allowed to re-grow for 1 h, and induced by adding isopropyl-thiogalactopyranoside to 1 mM final concentration. Cells are then harvested by centrifugation after 3 h and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having pullulanase activity, wherein the nucleotide sequence encoding a polypeptide and the nucleotide sequence of SEQ ID NO:7 have at least 90% sequence identity, or
   (b) the complement of the nucleotide sequence.

2. The polynucleotide of claim 1, wherein the nucleotide sequence encoding a polypeptide and the nucleotide sequence of SEQ ID NO:7 have at least 95% sequence identity.

3. The polynucleotide of claim 1, wherein the nucleotide sequence encoding a polypeptide comprises the nucleotide sequence of SEQ ID NO:7.

4. The polynucleotide of claim 1, wherein the polypeptide comprises the amino acid sequence of SEQ ID NO:8.

5. A vector comprising the polynucleotide of claim 1.

6. A chimeric gene comprising the polynucleotide of claim 1 operably linked to a regulatory sequence.

7. A method for transforming a cell comprising transforming a cell with the polynucleotide of claim 1.

8. A cell comprising the chimeric gene of claim 6.

9. A method for producing a plant comprising transforming a plant cell with the polynucleotide of claim 1 and regenerating a plant from the transformed plant cell.

10. A plant comprising the chimeric gene of claim 6.

11. A seed comprising the chimeric gene of claim 6.

* * * * *